(12) United States Patent
Ajiki et al.

(10) Patent No.: US 9,622,841 B2
(45) Date of Patent: Apr. 18, 2017

(54) TOOTH WHITENING APPARATUS AND TOOTH WHITENING METHOD

(71) Applicant: Panasonic Intellectual Property Management Co., Ltd., Osaka (JP)

(72) Inventors: Kaori Ajiki, Osaka (JP); Toshimitsu Minowa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 147 days.

(21) Appl. No.: 14/597,273

(22) Filed: Jan. 15, 2015

(65) Prior Publication Data

US 2015/0216642 A1      Aug. 6, 2015

(30) Foreign Application Priority Data

Jan. 31, 2014   (JP) ................. 2014-017116

(51) Int. Cl.
 *A61C 19/06* (2006.01)
 *A61C 1/00* (2006.01)
 *A61N 5/06* (2006.01)
 *A61C 13/15* (2006.01)

(52) U.S. Cl.
 CPC .......... *A61C 19/066* (2013.01); *A61C 1/0007* (2013.01); *A61C 19/003* (2013.01); *A61N 2005/0606* (2013.01)

(58) Field of Classification Search
 CPC ............... A61C 19/06; A61C 19/063
 USPC ...... 433/6, 29, 80, 215–216, 229; 606/2–19; 600/245, 246
 See application file for complete search history.

(56) References Cited

U.S. PATENT DOCUMENTS 6,976,841 B1 * 12/2005 Osterwalder ........ A61C 9/0006
                                                    433/29
2006/0127837 A1    6/2006 Nguyen et al.
(Continued)

FOREIGN PATENT DOCUMENTS

JP    2005-046421    2/2005
JP    2009-048837    3/2009
(Continued)

OTHER PUBLICATIONS

The Extended European Search Report dated May 29, 2015 for the related European Patent Application No. 15151586.3.
(Continued)

*Primary Examiner* — Nicholas Lucchesi
*Assistant Examiner* — Gwen M Demosky
(74) *Attorney, Agent, or Firm* — Greenblum & Bernstein, P.L.C.

(57) ABSTRACT

A tooth whitening apparatus is an apparatus that whitens a tooth surface with light. The tooth whitening apparatus includes a sheet member attachable to the tooth surface, a color tone sensor disposed on the sheet member and detecting a color tone of a portion of the tooth surface adjacent to the color tone sensor, and a light-emitting device disposed at a position on the sheet member corresponding to a position at which the color tone sensor is disposed, the light-emitting device irradiating the portion of the tooth surface adjacent to the color tone sensor with the light in accordance with a detection result of the color tone sensor.

4 Claims, 8 Drawing Sheets

(56) References Cited

U.S. PATENT DOCUMENTS

| | | | | |
|---|---|---|---|---|
| 2006/0234189 A1* | 10/2006 | Duret | ................... | A61C 19/066 |
| | | | | 433/215 |
| 2009/0058274 A1 | 3/2009 | Yokoyama et al. | | |
| 2009/0322227 A1* | 12/2009 | Jones | ................. | H05B 33/0803 |
| | | | | 315/76 |
| 2010/0305484 A1 | 12/2010 | Grollier et al. | | |
| 2015/0182758 A1* | 7/2015 | Ajiki | ................... | A61N 5/0616 |
| | | | | 607/88 |

FOREIGN PATENT DOCUMENTS

| | | |
|---|---|---|
| JP | 2011-505897 | 3/2011 |
| JP | 2013-168575 | 8/2013 |
| WO | 2013/039906 | 3/2013 |

OTHER PUBLICATIONS

Satoshi Aihara et al., "Trend in Research on Organic Imaging Devices" NHK Science & Technology Research Laboratories R&D No. 132, pp. 4-11, Mar. 2012.

* cited by examiner

FIG. 6

| BLOCK | COLOR TONE SENSOR UNIT | LIGHT-EMITTING DEVICE |
|---|---|---|
| FIRST BLOCK | FIRST AND SECOND COLOR TONE SENSOR UNITS | FIRST TO FOURTH LIGHT-EMITTING DEVICES |
| SECOND BLOCK | THIRD AND FOURTH COLOR TONE SENSOR UNITS | FIFTH TO EIGHTH LIGHT-EMITTING DEVICES |
| ⋮ | ⋮ | ⋮ |
| LTH BLOCK | ⋯ AND MTH COLOR TONE SENSOR UNITS | ⋯ TO NTH LIGHT-EMITTING DEVICES |

| 621 | 622 | 623 |
|---|---|---|
| COLOR TONE LEVEL | LIGHT BRIGHTNESS | TIME FOR WHICH LIGHT IS EMITTED |
| C0 | 0 | 0 |
| C1 | I1 | T1 |
| C2 | I2 | T2 |
| ⋮ | ⋮ | ⋮ |

TOOTH WHITENING APPARATUS AND TOOTH WHITENING METHOD

CROSS REFERENCES TO RELATED APPLICATIONS

The application claims priority to Japanese Patent Application No. 2014-017116 filed on Jan. 31, 2014, the content of which is hereby incorporated by reference.

BACKGROUND

1. Technical Field

The present disclosure relates to a tooth whitening apparatus and a tooth whitening method.

2. Description of the Related Art

Apparatuses that whiten the surfaces of teeth (or "tooth surfaces", below) by irradiating the tooth surfaces with light (such apparatuses are referred to as "tooth whitening apparatuses", below) have been developed (see, for example, Japanese Unexamined Patent Application Publication No. 2005-46421).

A tooth whitening apparatus described in Japanese Unexamined Patent Application Publication No. 2005-46421 irradiates the entirety of the oral cavity with predetermined light using a member shaped like a mouthpiece. After a predetermined chemical is applied to user's tooth surface, for example, he/she puts a mouthpiece-shaped member of the tooth whitening apparatus in his/her mouth and starts light emission of the tooth whitening apparatus. The chemical is activated as a result of the light emission and whitens the tooth surface to a degree according to the light intensity. Such an existing technology facilitates whitening of a tooth surface.

In the meantime, the color of the tooth surface may vary between teeth or portions of a tooth. For example, in order to uniform the color of teeth as much as possible to improve the appearance of the teeth, a highly discolored portion could be more actively irradiated with light. In other words, for effective whitening of a tooth surface, irradiating tooth by tooth or portion by portion of a tooth with light at the intensity corresponding to the requirement for whitening of each tooth or portion (intensity of light that is emitted and time for which light is emitted) is desirable.

However, the above-described existing technology is not capable of adjusting the light intensity tooth by tooth or portion by portion of a tooth and thus is not capable of effectively whitening a tooth surface.

SUMMARY

One non-limiting and exemplary embodiment provides a tooth whitening apparatus that is capable of more effectively whitening a tooth surface.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a tooth whitening apparatus that whitens a tooth surface using light. The tooth whitening apparatus includes a sheet member attachable to the tooth surface, a color tone sensor that is disposed on the sheet member and detects a color tone of the tooth surface, and a light-emitting device that is disposed on the sheet member and that, in operation, irradiates the tooth surface with the light in accordance with a detection result of the color tone sensor.

The disclosed tooth whitening apparatus is capable of more effectively whitening a tooth surface.

These general and specific aspects may be implemented using a system, a method, and a computer program, and any combination of systems, methods, and computer programs.

BRIEF DESCRIPTION OF THE DRAWINGS

FIG. 6 illustrates an example of the contents of a block information table according to the second embodiment;

FIG. 7 illustrates an example of the contents of a control rule table according to the second embodiment.

DETAILED DESCRIPTION

Figure 1:
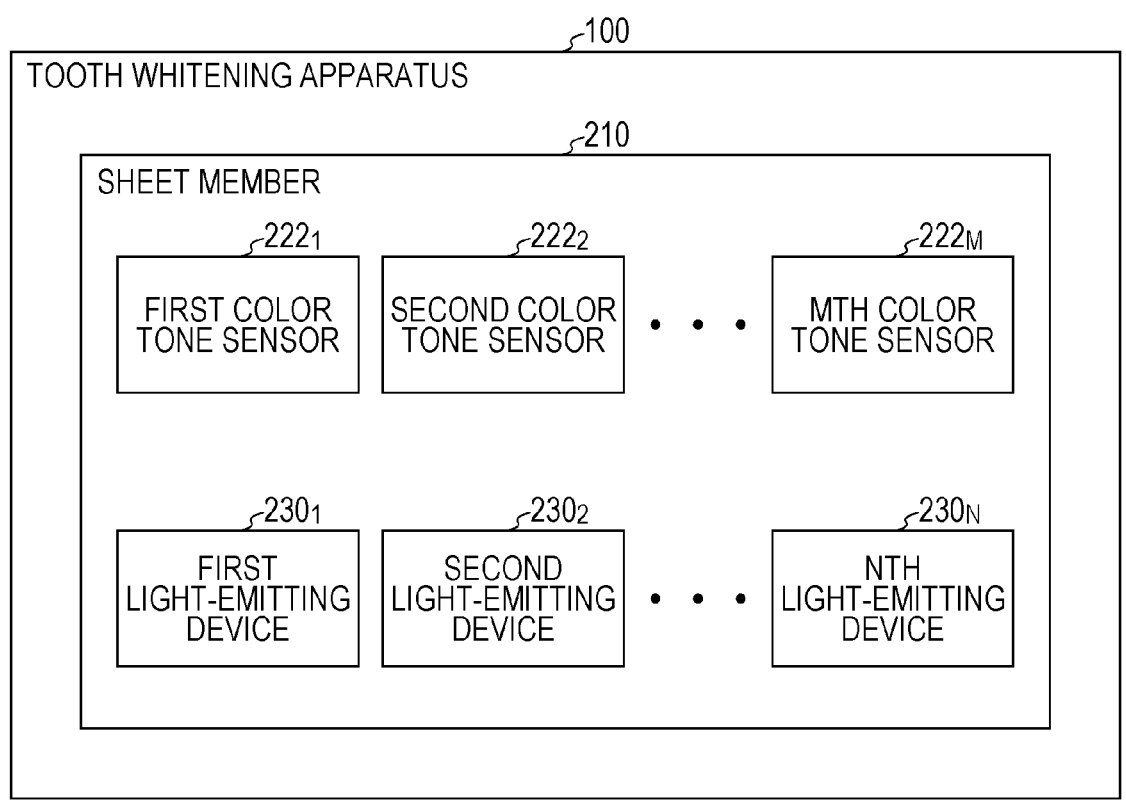
FIG. 1 illustrates an example of the configuration of a tooth whitening apparatus according to a first embodiment of the disclosure.

Referring now to the drawings, embodiments of the disclosure are described in detail below.

First Embodiment

A first embodiment of the disclosure is an example of a basic form of the disclosure.

FIG. 1 illustrates an example of the configuration of a tooth whitening apparatus 100 according to this embodiment.

The tooth whitening apparatus 100 illustrated in FIG. 1 is an apparatus that whitens a tooth surface using light. The tooth whitening apparatus 100 includes a sheet member 210, first to Mth (multiple) color tone sensors $222_1$ to $222_M$, and first to Nth (multiple) light-emitting devices $230_1$ to $230_N$.

The sheet member 210 is a member that is attachable to a tooth surface.

Each of the first to Mth color tone sensors $222_1$ to $222_M$ are disposed on the sheet member 210 to detect the color tone of the portion of the tooth surface adjacent to the color tone sensor.

The first to Nth light-emitting devices $230_1$ to $230_N$ are disposed at positions on the sheet member 210 corresponding to the positions at which the respective first to Mth color tone sensors $222_1$ to $222_M$ are disposed. The first to Nth light-emitting devices $230_1$ to $230_N$ irradiate portions of the tooth surface adjacent to the color tone sensors $222_1$ to $222_M$ with light for whitening in accordance with results detected by the corresponding color tone sensors $222_1$ to $222_M$.

Since the tooth whitening apparatus 100 can irradiate each portion of the tooth surface with light appropriate for the conditions of the portion, the tooth whitening apparatus 100 can effectively whiten the tooth surface.

The tooth whitening apparatus 100 may have one color tone sensor 222 on the sheet member 210 instead of multiple color tone sensors 222. The tooth whitening apparatus 100 may have one light-emitting device 230 instead of multiple light-emitting devices 230.

Second Embodiment

A second embodiment of the disclosure is an example of a specific form when the disclosure is applied to a sheet that can be attached to the entire tooth surface of upper front teeth facing the lip.

Appearance and Configuration of Tooth Whitening Apparatus

Firstly, the appearance and the configuration of a tooth whitening apparatus 100 according to the embodiment will be described.

Appearance of Tooth Whitening Apparatus

Figure 2:
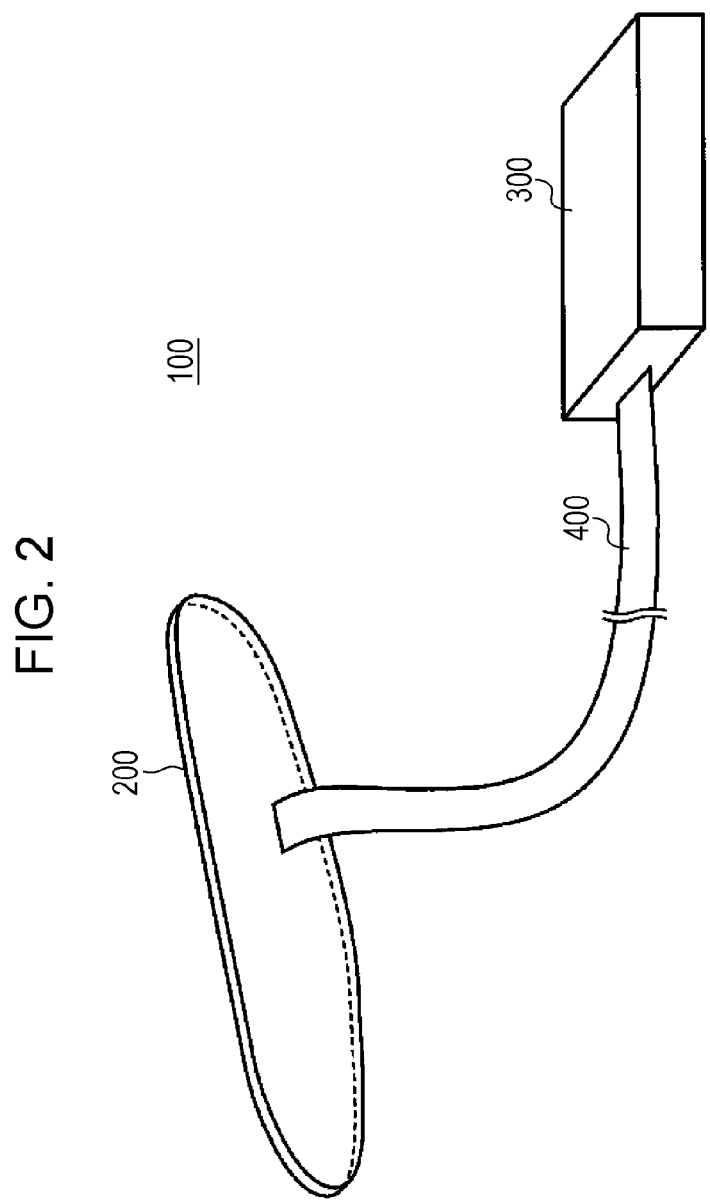
FIG. 2 illustrates an example of the appearance of a tooth whitening apparatus according to a second embodiment of the disclosure.

FIG. 2 illustrates the appearance of a tooth whitening apparatus 100 according to the embodiment.

As illustrated in FIG. 2, the tooth whitening apparatus 100 includes a sheet device 200 and a control unit 300.

Figure 3:
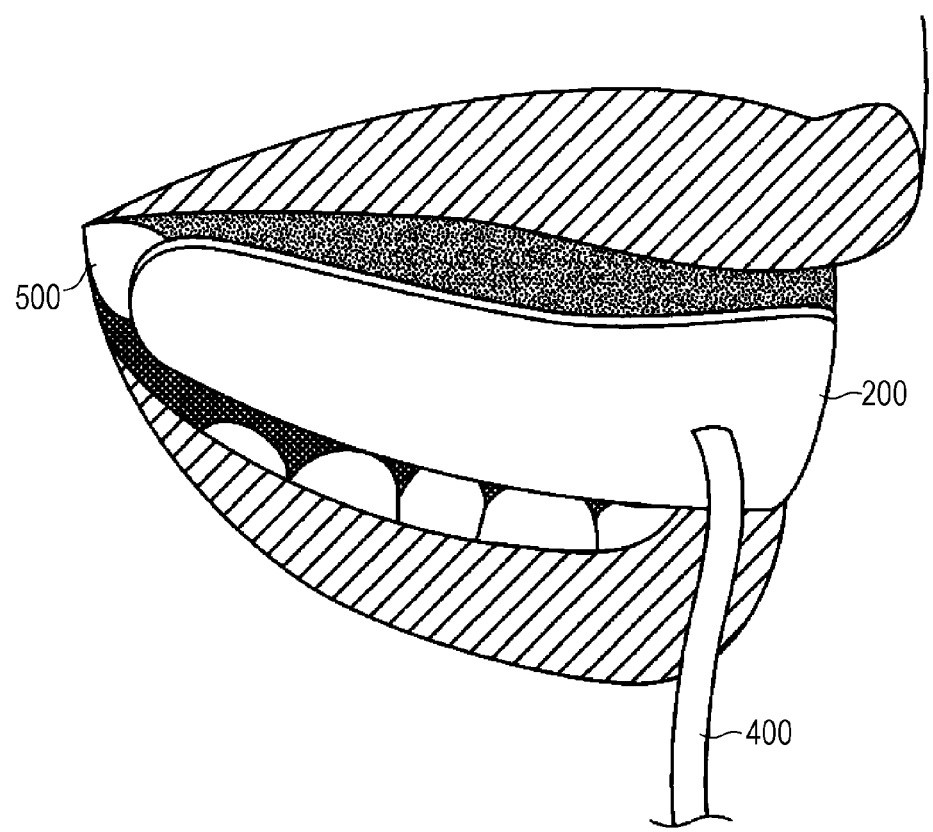
FIG. 3 illustrates an example of a sheet device according to the second embodiment that is in a used state.

The sheet device 200 is a sheet-like device sized so as to cover the entire tooth surface of the upper front teeth facing the lip (hereinafter referred to as "front-tooth region"). The base material of the sheet device 200 is a sheet member having elasticity and flexibility. The sheet device 200 is deformable in accordance with the three-dimensional shape of the tooth surface. FIG. 3 illustrates the state, as an example, in which the sheet device 200 is attached to the tooth surface of the front-tooth region.

A predetermined chemical (for example, titanium oxide), used as a photocatalyst in tooth whitening, is applied to the front-tooth region 500 in advance. As illustrated in FIG. 3, the sheet device 200 is attached to the front-tooth region 500 to which the chemical is applied. The sheet device 200 can keep being closely attached to the tooth surface of the front-tooth region 500 with the effect of the surface tension. For securing sufficient attachment, a biocompatible adhesive such as spirit gum, a silicone adhesive, or a latex adhesive may additionally be used.

The sheet device 200 can be selected from among multiple sizes in accordance with various sizes of the front-tooth region 500.

Multiple color tone sensor units and multiple light-emitting devices are disposed on the surface of the sheet member that is closely attached to the tooth surface, the sheet member serving as the base material. The configuration of the sheet device 200 including the arrangement of the color tone sensor units and the light-emitting devices are described in detail below.

Examples usable as the sheet member include a sheet member formed of a cured product of an energy-ray curable composition containing an acryloyl group-terminated urethane polymer and an acrylic monomer (see Japanese Unexamined Patent Application Publication No. 2013-168575).

The control unit 300 is a unit protected by a housing made of a material such as plastics. The control unit 300 has a function of controlling the operations of color tone sensor units 220 and light-emitting devices 230, which are described below. The control unit 300 is connected to the sheet device 200 with a cable 400(See Fig2. and FIG. 3).

Although not illustrated, the cable 400 includes signal lines that connect an operation determining unit 320 to the color tone sensor units 220 and the light-emitting devices 230. The cable 400 may have such a length that the control unit 300 can be held in a pocket of the user's clothes in the state, for example, where the sheet device 200 is attached to the tooth surface.

Configuration of Sheet Device

Figure 4:
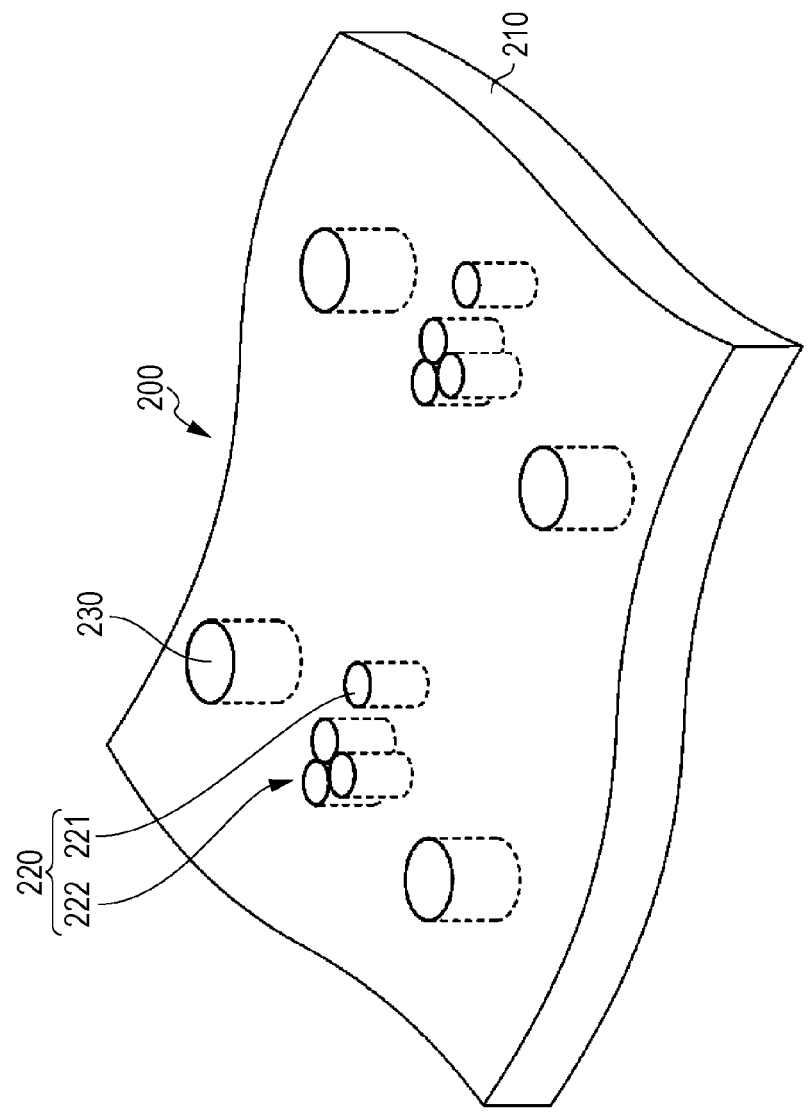
FIG. 4 illustrates an example of the configuration of the sheet device according to the second embodiment.

FIG. 4 illustrates an example of the configuration of the sheet device 200. FIG. 4 illustrates the main portion of the entire sheet device 200.

In FIG. 4, the sheet device 200 has a configuration in which color tone sensors 220 and light-emitting device units 500 are embedded in the sheet member 210.

Each color tone sensor unit 220 includes a detection light-emitting device 221, which outputs white light, and a color tone sensor 222, which receives light that has been reflected off the tooth surface after being output from the detection light-emitting device 221. A light emitting surface of the detection light-emitting device 221 and a light receiving surface of the color tone sensor 222 are exposed from the surface of the sheet member 210 that is closely attached to the tooth surface (hereinafter referred to as an "inner surface"). Specifically, the color tone sensor unit 220 detects the color tone of the adjacent portion of the tooth surface in a state where the sheet device 200 is attached to the front-tooth region.

However, the light receiving surface of the color tone sensor 222 may be positioned inward from the inner surface of the sheet member 210. For example, the color tone sensor 222 is positioned so that the light receiving surface is positioned approximately 100 micrometers away from the tooth surface in the state where the inner surface of the sheet member 210 is closely attached to the tooth surface.

The light emitting surface of the light-emitting device 230 is exposed from the inner surface of the sheet member 210. Specifically, the light-emitting device 230 irradiates the adjacent portion of the tooth surface with light in the state where the sheet device 200 is attached to the front-tooth region. The light-emitting device 230 is, for example, a light emitting diode (LED) that emits light of a predetermined wavelength for whitening (hereinafter referred to as "whitening light") or a light emitting unit that includes multiple LEDs. In this embodiment, the brightness of light emitted by the light-emitting device 230 is variable.

The detection light-emitting devices 221, the color tone sensors 222, and the light-emitting devices 230 may be sized as small as possible.

Examples usable as the small-sized color tone sensors 222 include a device that can capture three primary colors of RGB using an organic semiconductor described in "Trend in Research on Organic Imaging Devices" written by Satoshi AIHARA and Misao KUBOTA, in NHK Science & Technology Research Laboratories R&D No. 132, issued by NHK Science & Technology Research Laboratories, in Mar. 2012, pp. 4 to 11. The color tone sensor described in "Trend in Research on Organic Imaging Devices" written by Satoshi AIHARA and Misao KUBOTA, in NHK Science & Technology Research Laboratories R&D No. 132, issued by NHK Science & Technology Research Laboratories, in Mar. 2012, pp. 4 to 11 can be finely fabricated by printing.

Examples usable as the small-sized detection light-emitting devices 221 and light-emitting devices 230 include an organic LED formed by printing using a polymer described in Japanese Unexamined Patent Application Publication No. 2009-48837.

Unit by which Sheet Device is Controlled

In this embodiment, the operation of the sheet device 200 is controlled per each section obtained by dividing the sheet device 200 into multiple small sections with sides of several millimeters. Hereinbelow, each section of the sheet device 200 or each unit by which the sheet device 200 is controlled is called a "block".

At least one color tone sensor unit 220 and at least one light-emitting device 230 are disposed in each block. The color tone sensors 220 and the light-emitting devices 230 on the sheet device 200 may be arranged at a uniform density throughout the blocks, at different densities between different blocks, or at different densities within each block.

In this embodiment, L blocks are disposed in the sheet device 200 and multiple color tone sensor units 220 and multiple light-emitting devices 230 are allocated to each block. The L blocks have substantially the same area and the color tone sensors 220 and the light-emitting devices 230 are arranged at a substantially uniform density throughout the L blocks.

Functional Configuration of Tooth Whitening Apparatus

Figure 5:
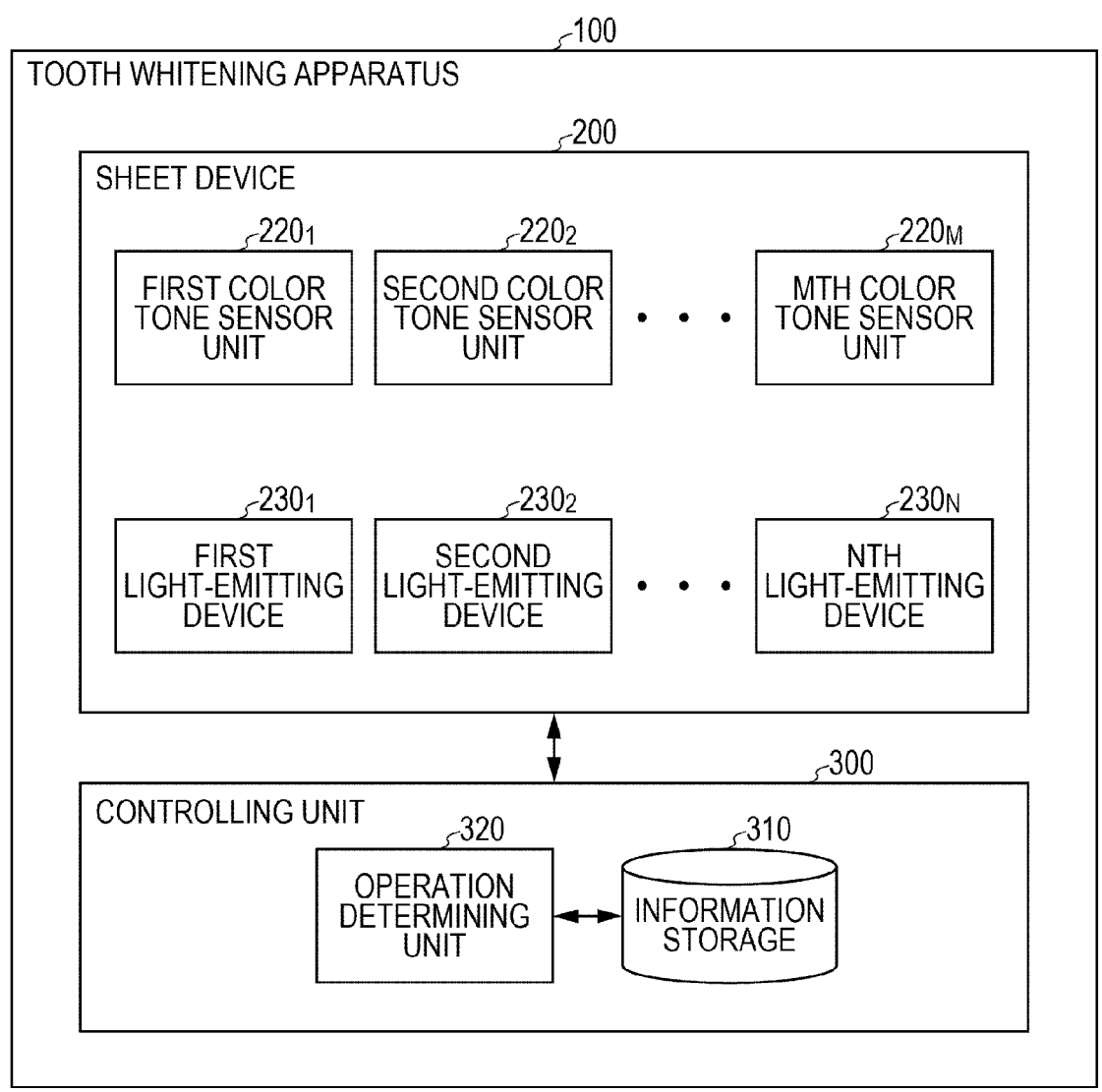
FIG. 5 illustrates an example of a functional configuration of a tooth whitening apparatus according to the second embodiment.

FIG. 5 illustrates an example of the functional configuration of the tooth whitening apparatus 100.

In FIG. 5, the tooth whitening apparatus 100 includes first to Mth color tone sensors $220_1$ to $220_M$ and first to Nth light-emitting devices $230_1$ to $230_N$, which are disposed on a sheet device 200, and an information storage unit 310 and an operation determining unit 320, which are disposed on a control unit 300.

The information storage unit 310 holds a block information table and a control rule table in advance. The block information table is a table that specifies which color tone sensor unit 220 and which light-emitting device 230 are allocated to which block. The control rule table is a table that specifies how each light-emitting device 230 is operated in accordance with a detection result of the corresponding color tone sensor unit 220.

FIG. 6 illustrates an example of the contents of the block information table.

As illustrated in FIG. 6, the block information table 610 specifies identifications 612 of color tone sensor units 220 disposed in respective blocks in association with identifications 611 of the blocks. The block information table 610 specifies identifications 613 of light-emitting devices 230 disposed in respective blocks in association with the identification 611 of the blocks.

For example, the identification 611 of a first block is associated with the identification 612 of first and second color tone sensor units $220_1$ and $220_2$ and the identification 613 of first to fourth light-emitting devices $230_1$ to $230_4$. This is because the first to fourth light-emitting devices $230_1$ to $230_4$ are disposed near the first and second color tone sensor units $220_1$ and $220_2$.

The area of the tooth surface over which the first and second color tone sensor units $220_1$ and $220_2$ can detect the color tone and the area of the tooth surface that the first to fourth light-emitting devices $230_1$ to $230_4$ can irradiate with white light coincide with each other. Thus, controlling the operation of each light-emitting device 230 on the basis of the detection results of the corresponding color tone sensor unit 220 per block, described above, enables irradiation of each portion with whitening light at an intensity corresponding to the necessity of the portion for whitening.

FIG. 7 illustrates an example of the contents of the control rule table.

As illustrated in FIG. 7, the control rule table 620 specifies a control value 622 corresponding to the brightness of light emitted by each light-emitting device 230 in association with the level 621 of values detected by the corresponding color tone sensor unit 220 (hereinafter referred to as a "color tone level"). The control rule table 620 also specifies a control value 623 corresponding to time for which the light emitting device 230 emits light in association with the color tone level.

An example of the color tone level 621 is the level of the depth of a color. The color of teeth greatly varies between individuals. Thus, the color tone level 621 may be defined as a relative level of the depth of a color using, for example, the mean color tone in the front-tooth region as a standard color tone. For example, the color tone level 621 of "C0" corresponds to the color of the tooth surface that is so white as not to require whitening and the color tone level 621 of "C1" corresponds to the color of the tooth surface that is relatively white but should receive whitening. The color tone level 621 corresponding to a deeper color is associated with the control value 622 having a higher brightness of light and a control value 623 having longer time for which light is emitted.

The control values 622 and 623 are appropriately determined on the basis of experiments and empirical rules on the assumption that, for example, all the blocks have substantially the same area, and the color tone sensor units 220 and the light-emitting devices 230 are arranged at substantially the same density throughout the blocks. The control values 622 corresponding to the brightness of light may differ between the light-emitting devices 230 or between blocks.

The operation determining unit 320 in FIG. 5 is connected to the first to Mth color tone sensors $220_1$ to $220_M$ and the first to Nth light-emitting devices $230_1$ to $230_N$ using the cable 400, which connects the control unit 300 and the sheet device 200 together, and signal lines (not illustrated) embedded in the sheet device 200. In other words, the operation determining unit 320 is capable of controlling the operation of the first to Mth color tone sensors $220_1$ to $220_M$ by outputting control signals to the first to Mth color tone sensors $220_1$ to $220_M$ and capable of inputting detection values output from the first to Mth color tone sensors $220_1$ to $220_M$. The operation determining unit 320 is also capable of controlling the operation of the first to Nth light-emitting device units $230_1$ to $230_N$ by outputting control signals to the first to Nth light-emitting device units $230_1$ to $230_N$.

The operation determining unit 320 determines, block by block, the operation of the light-emitting devices 230 disposed in each block of the sheet device 200 on the basis of detection values output from the corresponding color tone sensors 220 disposed in the block. At this time, the operation determining unit 320 determines the operation of each light-emitting device 230 with reference to the block information table 610 (see FIG. 6) and the control rule table 620 (see FIG. 7). The operation determining unit 320 then operates each light-emitting device 230 on the basis of the determined operation.

Although not illustrated, the control unit 300 includes, for example, a central processing unit (CPU), a storage medium such as a read only memory (ROM) in which a control program is stored, and an operation memory such as a random access memory (RAM). In this case, the function of each portion of the control unit 300 is implemented by the CPU executing the control program.

Although not illustrated, the control unit 300 includes a power source unit and an operation unit such as a key switch. The power source unit supplies power to operate the CPU and the sheet device 200. The operation unit receives various operations from a user, including an operation of starting light emission to the tooth surface.

The tooth whitening apparatus 100 having such a configuration is capable of irradiating each portion of the tooth surface with whitening light at an intensity appropriate for the portion.

Operation of Tooth Whitening Apparatus

Now, the operation of the tooth whitening apparatus 100 is described.

Figure 8:
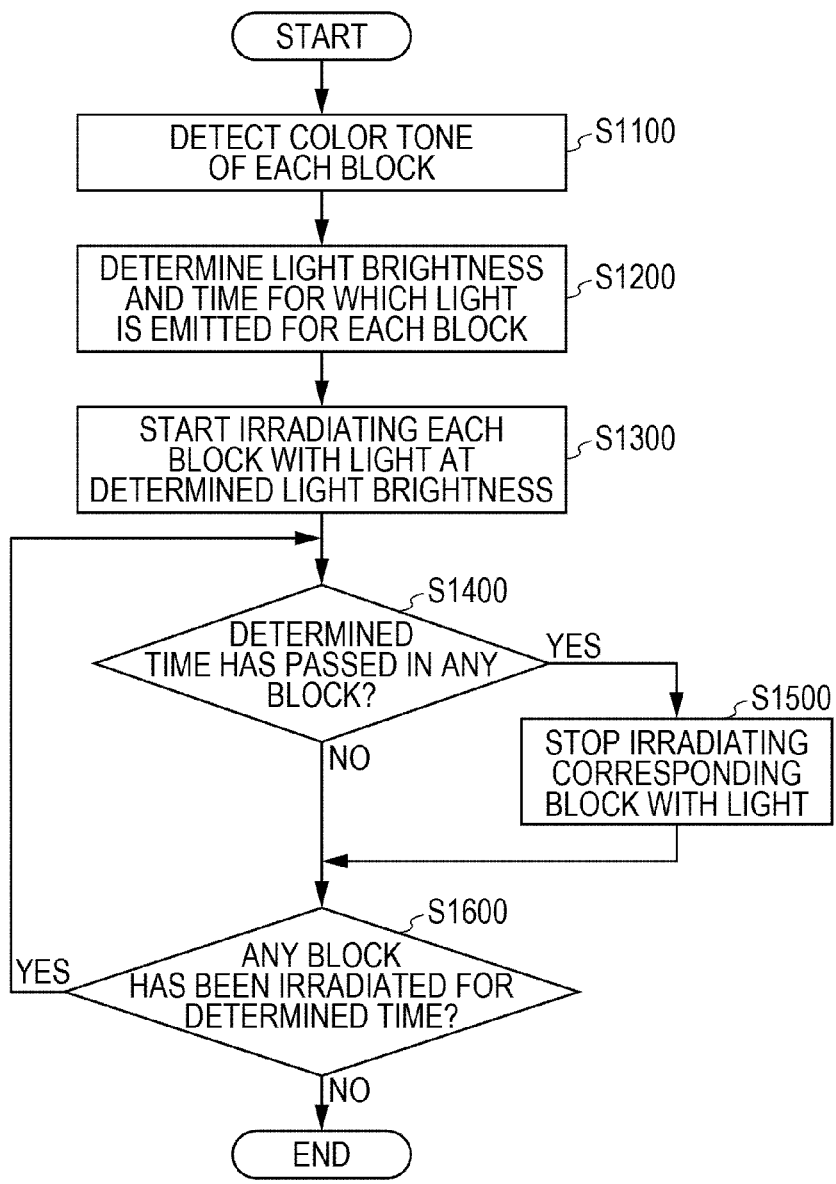
FIG. 8 is a flowchart illustrating an example of an operation of the tooth whitening apparatus according to the second embodiment.

FIG. 8 is a flowchart illustrating an example of the operation of the tooth whitening apparatus 100.

The tooth whitening apparatus 100 starts the following processing when a user instructs the tooth whitening apparatus 100 to start the operation in the state where the sheet device 200 is attached to the user's front-tooth region.

In Step S1100, each of the first to Mth color tone sensors $220_1$ to $220_M$ detect the color tone of the portion of the tooth surface adjacent to the color tone sensor and output the measured result to the operation determining unit 320.

In Step S1200, the operation determining unit 320 calculates, block by block, the mean value of the detection results detected by the multiple color tone sensor units 220 allocated to each block (hereinafter the mean value is referred to as a "block detection value"). With reference to the control rule table 620, the operation determining unit 320 determines, as a specific control applied to each block, the control value 622 of the brightness of light and the control value 623 of the time for which light is emitted (see FIG. 7) associated with the color tone level corresponding to the block detection value for the block. Here, the mean value of the detection results is used for the purpose of obtaining highly reliable data.

In Step S1300, the operation determining unit 320 applies the determined specific control to each light-emitting device 230. Specifically, the operation determining unit 320 starts irradiation of each block with whitening light at the determined light brightness. The operation determining unit 320 also starts timekeeping using a timer (not illustrated) or the like.

In Step S1400, the operation determining unit 320 determines whether or not there is any block that is being irradiated with light and that has been irradiated for the determined time. In the case where there is any block that has been irradiated for the determined time (YES in S1400), the processing of the operation determining unit 320 proceeds to Step S1500. In the case where there is no block that has been irradiated for the determined time (NO in S1400), the processing of the operation determining unit 320 proceeds to Step S1600.

In Step S1500, the operation determining unit 320 stops irradiating the block that has been irradiated for the determined time among the blocks that are being irradiated with light. Specifically, the operation determining unit 320 stops the light-emitting devices 230 allocated to the corresponding block from emitting light. Then, the processing of the operation determining unit 320 proceeds to Step S1600.

In Step S1600, the operation determining unit 320 determines whether or not there is any block that is being irradiated with light. When there is any block that is being irradiated with light (YES in S1600), the processing of the operation determining unit 320 returns to Step S1400. When there is no block that is being irradiated with light (NO in S1600), the processing of the operation determining unit 320 is finished.

In this manner, the tooth whitening apparatus 100 can control the operation of each light-emitting device 230 so that the corresponding block is irradiated with whitening light at the intensity determined in accordance with the color tone of the tooth surface for the block.

Effect of Tooth Whitening Apparatus

In this manner, the tooth whitening apparatus 100 according to this embodiment can irradiate each portion of the tooth surface with light at the intensity appropriate for the color tone of the portion.

Thus, the tooth whitening apparatus 100 according to this embodiment can whiten the entire front-tooth region in balance even in the case where the color of the tooth surface varies between teeth or portions of a tooth. In other words, the tooth whitening apparatus 100 according to the embodiment can effectively whiten the tooth surface.

The tooth whitening apparatus 100 according to the embodiment is also capable of emitting whitening light without the user holding the device with his/her hands. Thus, the user can use the tooth whitening apparatus 100 while performing other operations.

The tooth whitening apparatus 100 according to the embodiment is capable of saving power consumption to obtain the same irradiance since the distance from the light source that emits whitening light to the tooth surface is short, whereby the tooth whitening apparatus 100 can perform whitening in an environment-friendly manner.

Modified Example of Tooth Whitening Apparatus

The detection light-emitting device 221 of each color tone sensor unit 220 is not essential. For example, a common light source that outputs white light may be provided in the control unit 300 or in another component and white light may be distributed to each block through an optical fiber.

The operation determining unit 320 may use the intensity of light or the time for which light is emitted as a fixed value and may adjust the other one in accordance with the color tone. Alternatively, the operation determining unit 320 may determine whether each block is to be irradiated with light. The operation determining unit 320 may cause each light-emitting device 230 to cyclically blink and may control the blinking cycle or the duty ratio in accordance with the detection results of the corresponding color tone sensor unit 220.

The control unit 300 may be so shaped as to be wearable at, for example, the head, the earlobe, or the neck. The control unit 300 may include a strap that the user can hang around his/her neck. Alternatively, the control unit 300 may be used while being held in the oral cavity, for example, may be integrated with the sheet device 200.

The sheet device 200 may be sized smaller or larger than the one illustrated in FIG. 3. The control unit 300 may be connected to a sheet device 200 attached to an upper front-tooth region and a sheet device 200 attached to a lower front-tooth region.

In the case where the sheet device 200 is highly water resistant, the user can use the tooth whitening apparatus 100 while holding water in his/her oral cavity. In this case, the temperature of the oral cavity can be prevented from rising excessively high as a result of the light emission of the light-emitting device 230.

Part or the entirety of the functions of the control unit 300 according to the above-described second embodiment may be included in an apparatus that has another function as a main purpose such as a mobile phone.

The above-described functions may be implemented by a network server. Specifically, the function of a portion of the tooth whitening apparatus may be implemented by cloud computing. In this case, the operation determining unit needs to include at least a communication unit so as to transmit data of the color tone level of the tooth surface to the server and obtain the intensity of light and the time for which each block is irradiated with light.

The tooth whitening apparatus 100 may include an operation determining unit 320 for each block, the operation determining unit 320 performing operations for the corresponding block.

A tooth whitening apparatus according to the disclosure is a tooth whitening apparatus that whitens a tooth surface using light. The tooth whitening apparatus includes a sheet member attachable to the tooth surface, a color tone sensor that is disposed on the sheet member and detects a color tone of the tooth surface, and a light-emitting device that is disposed on the sheet member that, in operation, irradiates the tooth surface with the light in accordance with a detection result of the color tone sensor.

The tooth whitening apparatus may also include a detection light-emitting device that irradiates the tooth surface with light for the color tone sensor to detect the color tone.

The tooth whitening apparatus may also include a plurality of color tone sensors that include the color tone sensor disposed on the sheet member, and a plurality of light-emitting devices that include the light-emitting device disposed on the sheet member, and the plurality of light-emitting devices operating in accordance with detection results of the color tone sensors, respectively.

In the tooth whitening apparatus, the sheet member may be attachable to tooth surfaces of a plurality of adjacent front teeth facing a lip.

In the tooth whitening apparatus, the plurality of color tone sensors and the plurality of light-emitting devices may be disposed in a plurality of sections of the sheet member, and the tooth whitening apparatus may further include an operation determining unit that, in operation, determines, section by section, an operation of at least one of the light-emitting devices disposed in each section on the basis of a detection result of at least one of the color tone sensors disposed in the section.

In the tooth whitening apparatus, the operation determining unit may adjust at least one of brightness of light emitted by the at least one of the light-emitting devices and time for which the at least one of the light-emitting devices emits light in accordance with a detection result of the at least one of the color tone sensors.

A method for whitening a tooth according to the disclosure is a method for whitening a tooth surface using light. The method includes operating a color tone sensor disposed on a sheet member attachable to the tooth surface to detect a color tone of the tooth surface, and operating a light-emitting device in accordance with a detection result of the color tone sensor to irradiate the tooth surface, the light-emitting device being disposed on the sheet member. A tooth whitening apparatus according to the disclosure is a tooth whitening apparatus that includes a sheet attachable to a tooth surface including a first tooth surface area and a second tooth surface area, the sheet including a first portion and a second portion, a color tone sensor disposed at the first portion, the color tone sensor detecting a color tone around the first tooth surface area, and a light-emitting device disposed at the second portion, the light-emitting device irradiating the second tooth surface area with light in accordance with the detected color tone.

The present disclosure is usable as a tooth whitening apparatus that can effectively whitens a tooth surface and a tooth whitening method with which a tooth surface can be effectively whitened.

What is claimed is:

1. A tooth whitening apparatus, comprising:
   a sheet member attachable to a tooth surface;
   a color tone sensor unit that is disposed on the sheet member, the color tone sensor unit including a detection light-emitting device outputting light being reflected on the tooth surface and a color tone detector receiving resulting light from the reflection on the tooth surface, the color tone sensor unit thereby obtaining a detection of a color tone of the tooth surface; and
   an irradiation light-emitting device, different from the detection light-emitting device, that is disposed on the sheet member and that emits irradiation light toward the tooth surface, wherein the irradiation light emitted by the irradiation light-emitting device is emitted at a determined brightness and for a determined time period after the color tone sensor unit obtains the detection; and
   an operation determining unit that determines, before the irradiation light-emitting device emits the irradiation light, the brightness and the time period on the basis of the detection by the color tone sensor unit.

2. The tooth whitening apparatus according to claim 1, wherein the sheet member is attachable to tooth surfaces of a plurality of adjacent front teeth facing a lip.

3. The tooth whitening apparatus according to claim 1, wherein
   the color tone sensor unit includes a plurality of color tone sensor units disposed on the sheet member; and
   the irradiation light-emitting device includes a plurality of irradiation light emitting devices, the plurality of irradiation light emitting devices being different from a plurality of detection light-emitting devices of the plurality of color tone sensor units, wherein the plurality of irradiation light-emitting devices are disposed on the sheet member,
   wherein the sheet member includes a first area and a second area different from the first area,
   wherein the first area includes at least a first one of the plurality of color tone sensor units and at least a first one of the plurality of irradiation light-emitting devices,
   wherein the second area includes at least a second one of the plurality of color tone sensor units and at least a second one of the plurality of irradiation light-emitting devices, and
   wherein each of the plurality of color tone sensor units is configured to detect a color tone of a corresponding tooth surface.

4. A method, comprising:
   outputting, by a detection light-emitting device disposed on a sheet member, light being reflected on a tooth surface;
   performing, by a color tone detector disposed on the sheet member, a receiving of resulting light from the reflection on the tooth surface, and a color tone sensor unit, including the detection light-emitting device and the color tone detector, thereby obtaining a detection of a color tone of the tooth surface;
   emitting, by an irradiation light-emitting device different from the detection light-emitting device and disposed on the sheet member, irradiation light toward the tooth surface and at a determined brightness and for a determined time period after the color tone sensor unit obtains the detection; and
   determining, before the irradiation light-emitting device emits the irradiation light, the brightness and the time period on a basis of the detection by the color tone sensor unit.

* * * * *